(12) United States Patent
Masson et al.

(10) Patent No.: US 6,409,731 B1
(45) Date of Patent: Jun. 25, 2002

(54) BONE LEVELER APPARATUS

(75) Inventors: Marcos V. Masson; Mark Henry, both of Houston, TX (US)

(73) Assignee: Global Orthopaedic Solutions, L.L.C., Houston, TX (US)

( * ) Notice: Subject to any disclaimer, the term of this patent is extended or adjusted under 35 U.S.C. 154(b) by 0 days.

(21) Appl. No.: 09/916,832

(22) Filed: Jul. 30, 2001

(51) Int. Cl.[7] .................................................. A61F 5/00
(52) U.S. Cl. ..................... 606/86; 600/210; 600/217; 600/226; 600/227; 600/234; 600/235
(58) Field of Search ................................ 600/201, 210, 600/217, 219, 226, 227, 234, 235, 237; 606/86, 105

(56) References Cited

U.S. PATENT DOCUMENTS

| | | | | |
|---|---|---|---|---|
| 1,465,259 A | * | 8/1923 | Friedman | |
| 2,695,607 A | * | 11/1954 | Hipps et al. | ................. 600/210 |
| 3,463,144 A | * | 8/1969 | Hammond | ................... 600/210 |
| 3,731,673 A | * | 5/1973 | Halloran | |
| 3,916,879 A | * | 11/1975 | Cotten | |
| 4,747,395 A | * | 5/1988 | Brief | .......................... 600/210 |
| 4,995,875 A | * | 2/1991 | Coes | ...................... 600/210 X |
| 5,520,610 A | | 5/1996 | Giglio et al. | |
| 5,755,660 A | | 5/1998 | Tyagi | |
| 5,931,777 A | | 8/1999 | Sava | |
| 5,964,698 A | | 10/1999 | Fowler | |
| 6,074,343 A | | 6/2000 | Nathanson et al. | |
| 6,090,043 A | | 7/2000 | Austin et al. | |

FOREIGN PATENT DOCUMENTS

| | | | | |
|---|---|---|---|---|
| NL | 008000034 A | * | 8/1981 | ................. 600/217 |
| SU | 001220651 A | * | 3/1986 | ................. 600/210 |

* cited by examiner

*Primary Examiner*—Jeffrey A. Smith
(74) *Attorney, Agent, or Firm*—Harrison & Egbert

(57) ABSTRACT

A bone leveler or apparatus including a first blade member having a forward end suitable for contacting the bone and a rearward end, a second blade member having a forward end suitable for contacting the bone and a rearward end, and an elastic member having one end received by the first blade member and an opposite end received by a second blade member. Each of the blade members has an identical configuration. Each of the blade members has a hole formed between the forward end and rearward end. The elastic member has one end received by the hole of the first blade member and an opposite end received by the hole of the second blade member. Each of the blade members has a slot formed at the rearward end so as to extend inwardly therefrom. The respective ends of the elastic members are fixed into the slots of the respective blade members. The elastic member is a length of surgical tubing.

18 Claims, 3 Drawing Sheets

BONE LEVELER APPARATUS

BACKGROUND OF THE INVENTION

1. Field of the Invention

The present invention relates to surgical retractors. More particularly, the present invention relates bone lever or bone leveler apparatus which are used to fix a position of the bone during a surgical procedure. Additionally, the present invention relates to circumferential retractors.

2. Description of Related Art

Surgical "retraction" is the drawing back of body tissue. When the operation involves making an incision, the incision itself often must be retracted. During surgery, internal organs, bones and tissues are intermittently retracted through the opening created in the retracted incision.

In certain surgeries, an assistant's fingers are used as retractor paddles. However, greater technical ease is available through the use of various mechanical retractor systems. Mechanical retractor systems can be divided into two major groups: externally mounted "fixed" to the operating table and self-retaining retractors.

Bone leveler devices are commonly used so as to fix the position of a bone during surgery. Often, during surgery, it is necessary to insert pins, bolts, screws, plates and other mechanical devices onto a patient's bone. Typically, the incision is made in the skin so as to access the bone. A bone leveler device can then be inserted through the incision so as to contact the surface of the bone so that the bone can be placed into a proper position for the insertion of surgical screws and other items. Unfortunately, existing bone leveler apparatus are often difficult to use and often obstruct the access by the surgeon to the bone. Typically, conventional bone leveler apparatus include mechanical structures which are placed above the incision and extend downwardly into the incision so as to keep the incision open while engaging the bone. It is often difficult for the surgeon to properly operate with such obstructions in front of the incision or the bone. These existing bone leveler apparatus are often difficult to use, very expensive and require sterilization after use.

In the past, various patents have issued relating to such retractors. For example, U.S. Pat. No. 5,520,610, issued on May 28, 1996 to Giglio, describes a "self-retaining retractor". This retractor includes flexible, resilient retractor paddles which can be placed into the incision. A rigid frame is provided which includes two interlocking halves laid longitudinally over the incision. The incision retractor paddles are manually clipped to each frame half, and then the frame halves are opened to the desired extent. The incision retractor paddles and the frame provide the apparatus with stability for retraction of internal organs and tissues through the open incision by the addition of mounting jigs containing adjustment posts onto mounting means which radiate outwardly from the frame.

U.S. Pat. No. 5,931,777, issued on Aug. 3, 1999 to G. A. Sava, teaches a tissue retractor with particular use in spinal surgery. This tissue retractor includes a pair of pivotally linked arms, each with a blade mounted thereto by a ball-and-socket so as to allow free movement to the blades relative of the arms. The blades have an anchoring end to anchor to the bone. The retractor is operable by placing the blades in a wound opening, securing the anchoring ends to a portion of the bone in a position apart from each other, and operating the retractor to cause the blades to separate and to retract tissues surrounding the wound opening by outward pivoting of the blades relative to the position of the anchoring ends.

U.S. Pat. No. 6,074,343, issued on Jun. 13, 2000 to Nathanson et al., describes a surgical tissue retractor comprised of a plurality of retractor blades that can be operated simultaneously. Right and left retractor blades are mounted on an actuator mechanism that spreads or expands the blades as a rotatable primary actuator knob is rotated. A third retractable arm is mounted for simultaneous operation with the right and left retractor blade or independent operation through a secondary rotatable actuator knob that extends or retracts a threaded shaft attached to the center retractor blade.

U.S. Pat. No. 6,090,043, issued on Jul. 18, 2000 to Austin et al, describes a tissue retractor including a hook, a handle and a elastomeric band. The hook has a tissue-engaging portion and is retained by the handle such that the tissue engaging portion extends from a first end of the handle. The handle end of the band is retained by a second end of the handle. The back has a longitudinal body and at least one hub disposed about the body.

It is an object of the present invention to provide a bone leveler apparatus that is particularly useful for surgical procedures.

It is another object of the present invention to provide a bone leveler apparatus which is easy to use and easy to adjust.

It is another object of the present invention to provide a bone leveler apparatus which is disposable.

It is still another object of the present invention to provide a bone leveler apparatus which provides the surgeon with automatic tension feedback.

It is still a further object of the present invention to provide a bone leveler apparatus which is relatively inexpensive and easy to manufacture.

These and other objects and advantages of the present invention will become apparent from a reading of the attached specification and appended claims.

BRIEF SUMMARY OF THE INVENTION

The present invention is a bone leveler apparatus comprising a first blade member having a forward end suitable for contacting the bone and a rearward end, a second blade member having a forward end suitable for contacting the bone and a rearward end, and an elastic member having one end received by a first blade member and an opposite end received by the second blade member.

Each of the blade members has an identical configuration. Each of the blade members has a hole formed therein between the forward and rearward ends. The elastic member has one end extending through the hole of the forward end and an opposite end extending through the hole of the second blade member. Each of the blade members has a planar portion adjacent to the rearward end. The hole extends through this planar portion. Each of the blade member has a slot formed at the rearward end so as to extend rearwardly therefrom. One end of the elastic member is fixed in the slot of the first blade member. The opposite end of the elastic member is fixed in the slot of the second blade member. The slot is tapered so as to have a wide end opening at the rearward end and a narrow end adjacent to the hole. The forward end of each of the blade members has a pair of fingers formed thereat and extending in spaced relationship to each other. This forward end has a U-shaped channel formed between the pair of fingers. This U-shaped channel extends inwardly from the forward end. The pair of fingers are generally curved and extends outwardly in offset relationship to the planar portion of the respective blade member. The elastic member is a length of surgical tubing. In the preferred embodiment of the present invention, the elastic member is formed of latex-free surgical tubing. Typically, the length of surgical tubing should have a length generally matching the circumference of the limb or body portion onto which the bone leveler apparatus is applied.

BRIEF DESCRIPTION THE DRAWINGS

DETAILED DESCRIPTION OF THE INVENTION

Figure 1:
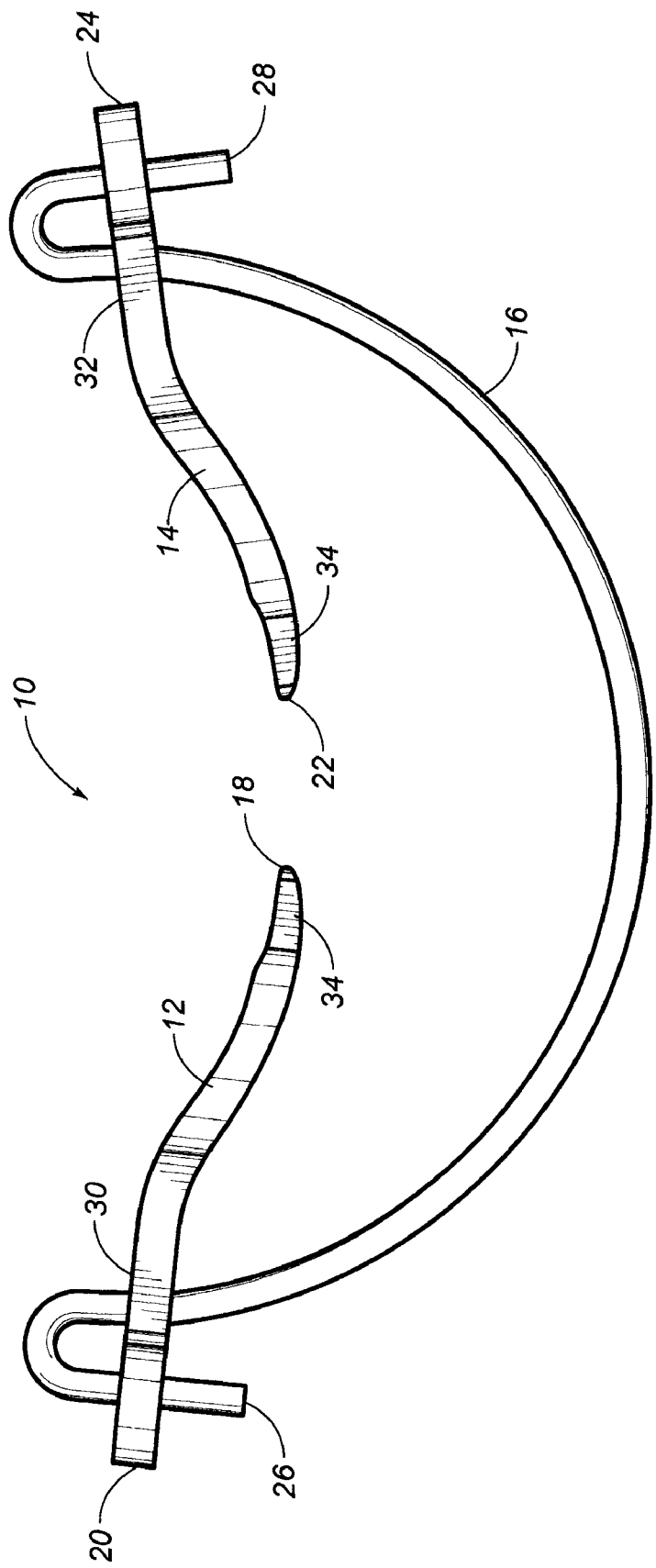
FIG. 1 is a side elevational view showing the bone leveler apparatus in accordance with the teachings of the preferred embodiment of the present invention.

Referring to FIG. 1, there is shown the bone leveler apparatus 10 in accordance with the teachings of the present invention. The bone leveler apparatus 10 includes a first blade member 12, a second blade member 14 and an elastic member 16. The first blade member 12 has a forward end 18 and a rearward end 20. The second blade member 14 has a forward end 22 and a rearward end 24. The elastic member 16 has one end 26 that is received by the first blade member 12 and an opposite end 28 that is received by the second blade member 14.

As can be seen in FIG. 1, each of the blade members has a generally identical configuration. In particular, the first blade member 12 has a planar portion 30 extending inwardly from the rearward end 20. A suitable hole is formed in this planar portion 30 so that the elastic member 16 can extend therethrough. Similarly, the second blade member 14 has a planar portion 32. A suitable hole was formed in the planar portion 32 so as to allow the opposite end 28 of the elastic member 16 to extend therethrough.

In order to fix the elastic member 16 relative to the blade members 12 and 14, a slot is formed so as to extend inwardly from the rearward end 20 of the first blade member 12 and the rearward end 24 of the second blade member 14. In actual use, after the end 26 has been threaded through the hole in the planar portion 30 of the first blade member 12, the end 26 of the elastic member 16 is pushed into the slot extending inwardly from the rearward end 20. The compression of the elastic member 16 in the slot of the first blade member 12 will fix the end 26 into position. A similar procedure is carried out with respect to the second blade member 14. As can be seen in FIG. 1, the opposite end 28 of the elastic member 16 is fixed in position in the slot which extends inwardly from the rearward end 24 of the second blade member 14.

In FIG. 1, it can be seen that the first blade member 12 has a forward end 18 which is suitable for contacting the bone during a bone leveling procedure. The forward end 18 includes fingers 34 which are generally curved and extend from the planar portion 30. The forward end 22 of the second blade member 14 also includes fingers 36 which are generally curved and extend outwardly from the planar portion 32. The fingers 34 and 36 are offset from the plane of the planar portions 30 and 32, respectively.

Figure 2:
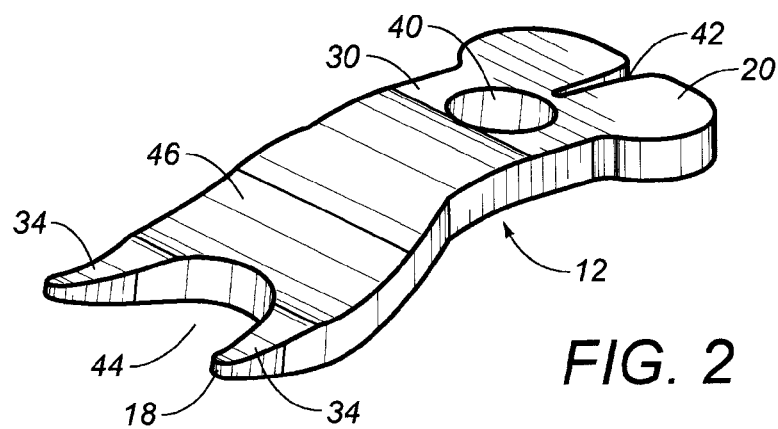
FIG. 2 is a perspective view of the bone leveler blade member as used in the present invention.

FIG. 2 shows an isolated view of the first blade member 12. The first blade member 12 is illustrated as having a hole 40 formed in the planar portion 30 and inwardly of the rearward end 20. The hole 40 will extend transverse to the plane of the planar portion 30. Hole 40 should have a diameter generally matching the diameter of the surgical tubing that is used for the elastic member 16.

A slot 42 is formed at the rearward end 20. The slot 42 is tapered so as to have a wide end at the rearward end 20 and a narrow end adjacent to the hole 40. When the surgical tubing of the elastic member 16 is placed into the slot 42, the surgical tubing will remain in place because of the compressive interference-fit relationship between the exterior of the surgical tubing of the elastic member 16 and the narrow end of the slot 42.

It can be seen that the first blade member 12 has fingers 34 formed at the forward end 18. A U-shaped channel 44 is formed between the pair of fingers 44 and extends inwardly from the forward end 18. The fingers 34 are particularly configured so as to properly grasp a surface of a bone. The curved section 46 extending from the fingers 34 to the planar portion 30 is configured so as to provide proper leverage to the surgeon. As such, this curved section 46 allows each of the blade members 12 and 14 to minimal deflection during surgery.

The blade member 12 should preferably be formed of a polycarbonate or LEXAN (TM) material. Ideally, the material used for the blade member 12 should be clear so that the surgeon can see through the blade member 12 during the surgical procedure. The material used for the blade member 12 is sterilizable and autoclavable. However, in the preferred embodiment of the present invention, the configuration of the blade member 12, along with the surgical tubing used for the elastic member 16, is disposable and of minimal cost.

Figure 3:
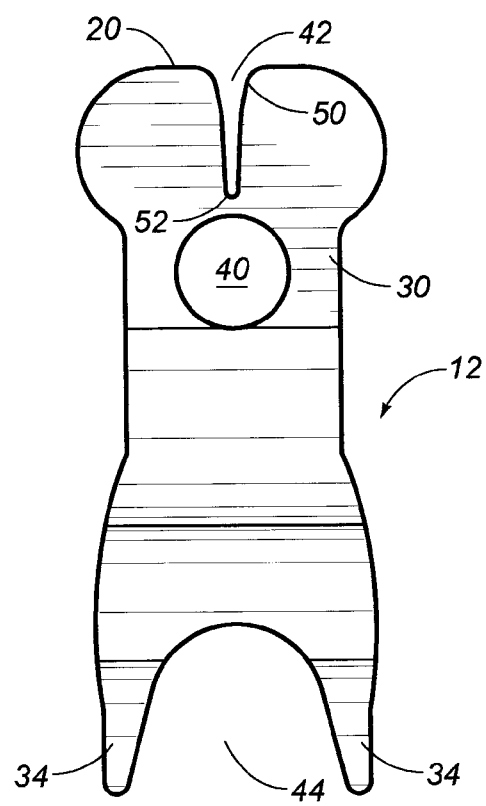
FIG. 3 is a plan view of the bone leveler blade member as used in the present invention.

FIG. 3 is a plan view of the blade member 12. Importantly, the blade member 12 has the same construction as blade member 14. As such, the manufacture of a single blade member will accomplish the purposes of forming both of the blade members 12 and 14. Blade member 12 is shown as having a circular hole 40 extending with its axis transverse to the plane of planar portion 30. Slot 42 is illustrated as having a wide end 50 adjacent to the rearward end 20 of blade member 12. Slot 42 has a narrow end 52 adjacent to the hole 40. The hole 42 is suitably tapered so that the end 26 of the surgical tubing of the elastic member 16 will be forced and fixed into position by residing adjacent to the narrow end 52.

FIG. 3 shows that the fingers 34 have a generally U-shaped construction. The U-shaped channel 44 extends between the fingers 34. The use of the U-shaped channel 44 and the fingers 34 minimizes damage to the tissues during the use of the bone lever tool of the present invention.

Figure 4:
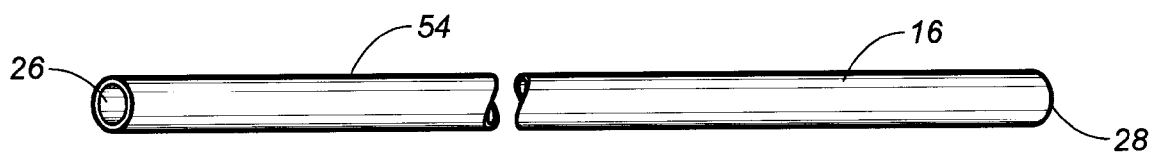
FIG. 4 is a perspective view of a length of surgical tubing used with the bone leveler apparatus of the present invention.

FIG. 4 is an isolated view showing the preferred embodiment of the elastic member 16. As can be seen, the elastic member 16 is a length of surgical tubing 54 having a first end 26 and an opposite end 28. The end 26 will be received within the slot 42 formed on the first blade member 12. Similarly, the end 28 will be received within the slot formed on the end of the second blade member 14. It has been found that surgeons are very familiar with the elasticity of the surgical tubing. As such, the use of the surgical tubing 54 is very compatible with surgical procedures. Ideally, the material for the surgical tubing 54 should be latex-free so as to avoid allergic reactions. The use of such surgical tubing provides an automatic feedback to the surgeon of the tensioning of the tubing 54 during the bone leveling procedure. As such, unlike prior art retractors, the surgeon will immediately know how much tension is required to move the bone to its desired position and can achieve such tension by simply creating more tension in the length of surgical tubing 54 prior to securing it into the respective slots of the blade members 12 and 14.

Figure 5:
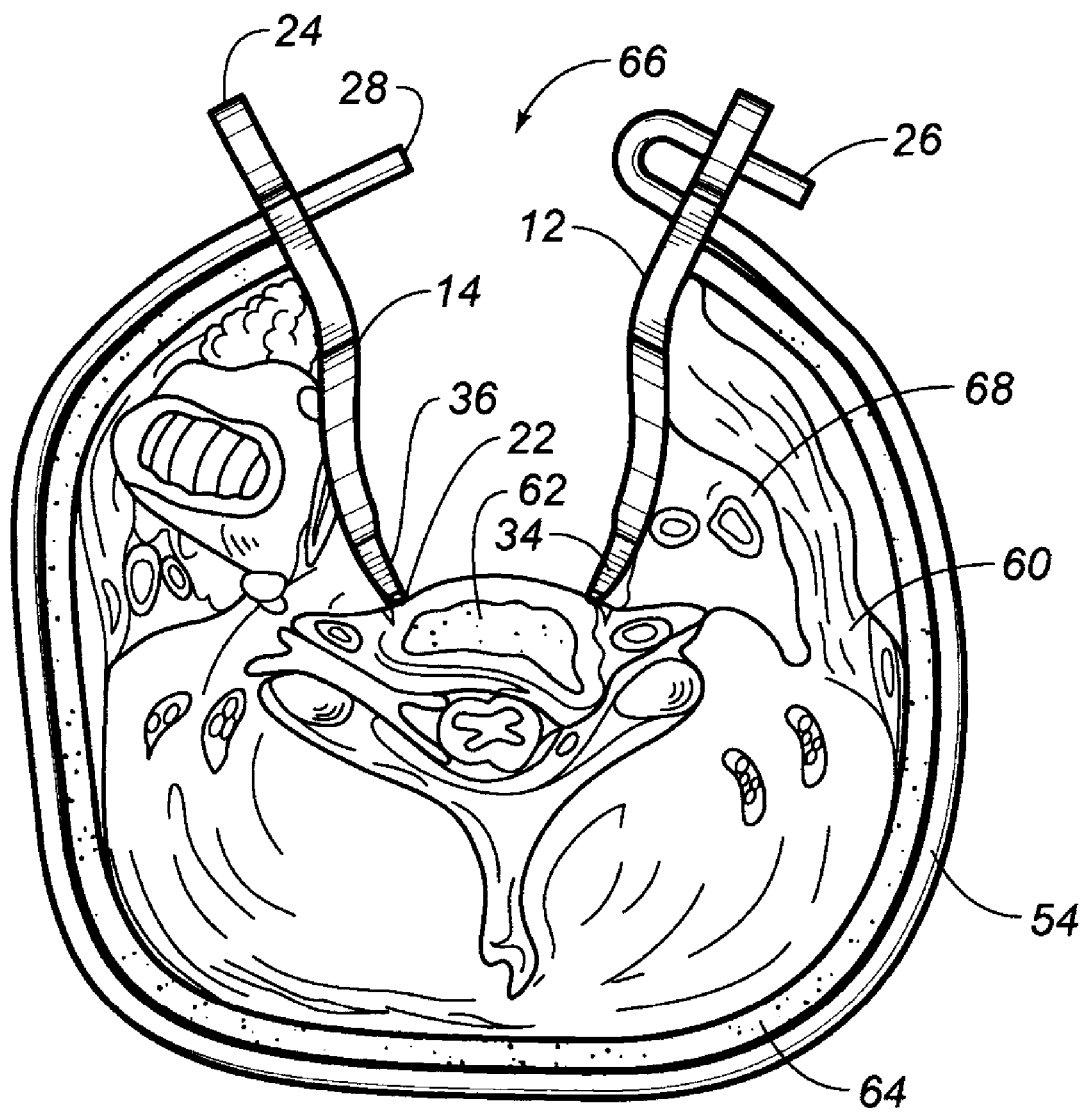
FIG. 5 is a cross-sectional view showing the application of the bone leveler apparatus during a surgical procedure.

FIG. 5 shows the operation of the bone leveler apparatus of the present invention. In FIG. 5, there is a limb 60 having a bone 62 therein. Flesh 64 will surround the limb 60. An incision 66 is formed in the skin 64 and into the flesh 68 of the limb 60. This incision will be suitable so as to extend toward the bone 62. The blade members 12 and 14 are inserted into the incision 66 and extend downwardly so that the forward end 18 of the first blade member 12 and the forward end 22 of the second blade member 14 contact or engage the bone 62. If proper pressure is applied to the blade members 12 and 14, the blade members will move along the periphery of the bone 62 so as to grasp the periphery of the bone 62 in the curved section adjacent to the fingers 34 of the first blade member 12 and the fingers 36 of the second blade member 14. As can be seen, the end 26 of the surgical tubing 54 (elastic member 16) is fixed into the slot 42 on the first blade member 12. The surgical tubing has been previously placed through the hole 40 of the first blade member 12. The end 26 is looped backwardly so as to be fixed into the slot 42 of the first blade member 12. The opposite end 28 of the surgical tubing 54 extends through the hole of the second blade member 14. The end 28 has not yet been fixed into position into the slot at the rearward end 24 of the second blade member 14.

During the surgical procedure, when the surgeon has determined that the blade members 12 and 14 have properly grasped the bone 62 and have moved the bone 62 to its desired position, the surgeon will simply grasp the end 28 of the surgical tubing 54, pull it forward to achieve the desired amount of tension, and then loop it rearwardly so that the end 28 will reside within the slot at the end 24 of the second blade member 14. As a result, consistent and proper tension will be immediately established so that the bone 62 will remain in its desired position during the surgical procedure.

When the surgical procedure is completed, the surgeon can simply remove one of the ends from their its slot in the blade members 12 and 14. As a result, the tension in the surgical tubing 54 will be released. The blade members 12 and 14 can then be pulled from the incision 66. The incision 66 can then be closed in accordance with the conventional practice. Following the surgical procedure, the blade members 12 and 14, along with the surgical tubing 54, can simply be disposed of in a conventional manner.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

We claim:

1. A bone lever apparatus comprising:
   a first blade member having a forward end suitable for contacting the bone and a rearward end;
   a second blade member having a forward end suitable for contacting the bone and a rearward end; and
   an elastic member having one end received by said first blade member and an opposite end received by said second blade member.

2. The bone lever apparatus of claim 1, each of said first and second blade members having an identical configuration.

3. The bone lever apparatus of claim 1, each of said first and second blade members having a hole formed therein and between said forward end and said rearward end, said elastic member having one end extending through said hole of said first blade member, said elastic member having said opposite end extending through said hole of said second blade member.

4. The bone lever apparatus of claim 3, each of said first and second blade members having a planar portion adjacent said rearward end, said hole extending through said planar portion.

5. The bone lever. apparatus of claim 3, each of said first and second blade members having a slot formed at said rearward end, said one end of said elastic member received in said slot of said first blade member, said opposite end of said elastic member received in said slot of said second blade member.

6. The bone lever apparatus of claim 5, said slot being tapered so as to have a wide end opening at said rearward end and a narrow end adjacent said hole.

7. The bone lever apparatus of claim 1, said forward end of each of said first and second blade members having a pair of fingers formed thereat and extending in spaced relationship to each other.

8. The bone lever apparatus of claim 7, said forward end of each of first and second blade member having a U-shaped channel formed between said pair of fingers, said U-shaped channel extending inwardly from said forward end.

9. The bone lever apparatus of claim 7, each of said first and second blade members having a planar portion adjacent said rearward end, said pair of fingers being curved and extending outwardly in offset relationship to said planar portion.

10. The bone lever apparatus of claim 1, said elastic member being a length of surgical tubing.

11. The bone lever apparatus of claim 10, said length of surgical tubing being latex-free.

12. A bone leveler comprising:
    a blade member having a forward end suitable for contacting the bone and a rearward end, said blade member having a hole formed therein between said forward end and said rearward end, said hole being suitable for receiving a portion of the surgical tubing therein, said blade member having a slot formed at said rearward end and extending inwardly from said rearward end, said slot being tapered so as to have a wide end opening at said rearward end and a narrow end adjacent said hole.

13. The bone lever tool of claim 12, said blade member having a planar portion adjacent said rearward end, said hole extending through said planar portion.

14. The bone lever tool of claim 12, said forward end of said blade member having a pair of fingers formed thereat and extending in spaced relationship to each other.

15. The bone lever tool of claim 14, said forward end of said blade member having a U-shaped channel formed between said pair of fingers, said U-shaped channel extending inwardly from said forward end.

16. The bone lever tool of claim 14, said blade member having a planar portion adjacent said rearward end, said pair of fingers being curved and extending outwardly in offset relationship to said planar portion.

17. A bone lever tool comprising:
    a first blade member having a forward end suitable for contacting the bone and a rearward end, said first blade member having a hole formed therein between said forward end and said rearward end;

a second blade member having an identical configuration to said first blade member; and a length of surgical tubing having one end received by said hole of said first blade member and an opposite end received by said second blade member.

18. The bone lever tool of claim 17, each of said first and second blade members having a tapered slot formed at the respective rearward end thereof, the respective ends of said length of surgical tubing being fixed in the respective tapered slots of said first and second blade members.

* * * * *